(12) United States Patent
Chang

(10) Patent No.: US 6,183,705 B1
(45) Date of Patent: Feb. 6, 2001

(54) METHOD OF CLEANING AND DISINFECTING CONTACT LENS, AND APPARATUS THEREFOR

(76) Inventor: Ching-Tsai Chang, No. 17-4, Jin-Hua Street, Taipei (TW)

(*) Notice: Under 35 U.S.C. 154(b), the term of this patent shall be extended for 0 days.

(21) Appl. No.: 08/689,776

(22) Filed: Aug. 14, 1996

(51) Int. Cl.$^7$ ........................................ A61L 2/00
(52) U.S. Cl. .................. 422/301; 422/128; 422/20; 422/297; 134/901
(58) Field of Search ........................ 422/20, 28, 128, 422/297, 301; 134/1, 57 R, 19, 901

(56) References Cited

U.S. PATENT DOCUMENTS

| | | | |
|---|---|---|---|
| 3,973,760 | * | 8/1976 | Browning ................ 259/72 |
| 4,607,652 | * | 8/1986 | Yung ..................... 134/184 |
| 4,697,605 | * | 10/1987 | Yung ..................... 134/107 |
| 4,991,609 | * | 2/1991 | Browning ............. 134/57 R |
| 5,209,783 | * | 5/1993 | Huth et al. .............. 134/19 |

* cited by examiner

Primary Examiner—Lila Feisee
Assistant Examiner—Eliane Lazar-Wesley
(74) Attorney, Agent, or Firm—Smith, Gambrell & Russell, LLP

(57) ABSTRACT

A method of cleaning and disinfecting contact lenses, including the steps of a) transmitting a ultrasonic energy field toward a pair of contact lenses being suspended in a solution medium in a cleaning cup, causing a cavitation to be produced to remove dirt from the contact lenses; b) keeping the solution medium to be maintained standing still in for about 3–5 minutes for permitting suspended substance to settle to the bottom of the solution medium; c) using heating means to heat the solution medium to about 90° C. for about 15–20 minutes so as to disinfect bacteria and degrade toxic substance carried on the contact lenses; and d) gradually cooling down the temperature of the solution medium to room temperature. The invention relates also to the apparatus for the performance of the method which includes a ultrasonic wave guide and a control circuit board mounted in a housing, a serving container unit mounted in the ultrasonic wave guide to hold a lens holder in NaCl, permitting contact lenses to be cleaned by ultrasonic waves from a ultrasonic speaker and disinfected by heat from a heating rod.

5 Claims, 4 Drawing Sheets

METHOD OF CLEANING AND DISINFECTING CONTACT LENS, AND APPARATUS THEREFOR

BACKGROUND OF THE INVENTION

1. Field of the Invention

The present invention relates to a method of cleaning and disinfecting contact lenses which uses a ultrasonic speaker to produce ultrasonic waves for removing dirt from contact lenses, a heating rod to produce heat for sterilizing the contact lens serving solution medium.

2. Description of the Prior Art

Contact lenses have been widely accepted in recent years for the advantage of high convenience, and for some medical considerations for example, highly correcting effect on the deviation of the power of vision and slowing down the deterioration of the power of vision. However, contact lenses must be used subject to a critical hygienic rule, which may affect one's daily life. Before after wearing, contact lenses must be well cleaned and disinfected. When not in use, contact lenses must be well maintained so that the service life of contact lenses can be prolonged. Serving contact lenses is not an easy job. When contact lenses are in use, pollutant for example secretion in tears, dust in air, dirty substance on the skin of the hand or face, etc. may be accumulated on contact lenses, causing the eyes to be stimulated. In order to effectively remove pollutant from contact lenses and to disinfect bacteria, contact lenses are preferably cleaned and disinfected daily. A complete contact lens serving process includes the procedures of cleaning, disinfecting, and storing. Different methods and apparatus may be employed to achieve a complete contact lens serving process.

Conventionally, the cleaning of contact lenses is achieved by rubbing contact lenses with fingers in a cleaning solution. When rubbing a contact lens with fingers, the surface of the contact lens tends to he damaged. This cleaning method cannot only remove grease from the surface of the contact lens, however it cannot remove dirt and bacteria from the capillary tubes of the contact lens. Rubbing a contact lens witch fingers tend to cause the capillary tubes of the contact lens to be blocked up. When the capillary tubes of a contact lens are blocked up, the contact lens become turbid, and white spots may occur in the surface of the contact lens to reduce its air permeability and water absorbing ability.

There are mechanical apparatus controlled to produce a rotary or reciprocating motion, causing the cleaning solution to be stirred up to remove dirt from contact lenses, and apparatus controlled to generate ultrasonic waves, causing a cavitation to be produced to remove dirt from contact lenses. Chemical solutions may be used to dissolve deposits, causing it to leave from contact lenses. Chinese patent no. 75202938 discloses an automatic lens cleaner which comprises a motor a spinning lens holder turned by the motor in a solution trough. When in use the contact lenses must be washed in the cleaning solution in the solution trough through an oxidation or reduction action for at least 30 minutes. Therefore, the user must spend a lot of time in cleaning the contact lenses daily. Furthermore, if the contact lenses are not properly mounted in the spinning lens holder, they tend to be damaged during the spinning of the spinning lens holder.

When a ultrasonic cleaning apparatus is used, ultrasonic waves are transmitted to the cleaning solution to produce a cavitation in it, causing the cleaning solution to produce micro-jets for removing dirt from the contact lenses. This cleaning apparatus is effective and efficient, therefore it is widely accepted by ophthalmologists and professional organizations. However, this apparatus is heavy and expensive, not suitable for personal use.

Using a chemical solution to clean contact lenses has limitations. In order to protect the physical properties of contact lenses, the concentration of the chemical solution must be strictly limited. When cleaning, contact lenses must be dipped in the chemical solution for a long length of time for example from 2 to 12 hours. It is low efficient to spend such a long length of time daily in cleaning contact lenses. Furthermore, regular chemical solutions cannot effectively remove greasy substance or organic matter. In order to effectively clean contact lenses, several chemical solution may be used, thereby causing the cleaning cost unable to be reduced. When cleaning, chemical agent may pass to the inside of the capillary tubes. If the capillary tubes are not well washed, deposited chemical agent may hurt the user's eyes or cause the user's eyes to have an allergy.

When contact lenses are cleaned, a disinfecting procedure must be followed. The disinfecting procedure is to prevent after-effect resulted from enzymatic degradation. There are two methods adapted for achieving the disinfecting procedure, namely, the physical disinfecting method and the chemical disinfecting method. The physical disinfecting method is to sterilize contact lenses by heat or ultraviolet rays. The chemical disinfecting method is to dip contact lenses in a sterilizing solution, permitting organic matter to be killed in the sterilizing solution. Conventional apparatus for sterilizing contact lenses by heat are commonly designed for professional use only. These apparatus have numeral drawbacks as follows: (1) if contact lenses are heated before cleaning or when not well cleaned, protein in tears will be solidified and fixedly secured to the surface of the contact lenses, causing the color of the contact lenses to be changed and the transparency thereof to be reduced; (2) the service life of contact lenses will he shortened if the heating temperature is not well controlled; (3) a serving container means shall be separately used for carrying contact lenses when going outdoors; and (4) a chemical reaction tends to occur during the heating of the contact lenses if chemical solution is not well cleaned, thereby causing the material property of the contact lenses to be affected.

Using ultraviolet rays to sterilize contact lenses cannot eliminate the aforesaid drawbacks. When contact lenses are held in place, there are dead angles around the contact lenses in which ultraviolet rays cannot reach. Therefore, ultraviolet rays cannot effectively sterilize contact lenses. Furthermore, this sterilizing method takes much time.

Because conventional sterilizing apparatus for sterilizing contact lenses by heat or ultraviolet rays are designed for professional use only, most contact lens users use chemical solutions to sterilize contact lenses. However, using chemical sterilizing solutions to sterilize contact lenses wastes much time for example more than 4 hours. These chemical sterilizing solutions commonly contain substance molecules such as chlorohexidine, thimerosal, sorbic acid, hydrogen peroxide, etc. If these molecules are not completely neutralized or removed after the sterilizing procedure, they will injure the cells of the eyes. Because the size of these molecules is tiny and smaller than the inner diameter of the capillary tubes of the contact lenses, they tend to pass to the inside of the capillary tubes, causing the contact lenses to change color, and causing the user to have an allergic reaction when wearing the contact lenses. Furthermore, the expense of the chemical sterilizing solution is another burden to the user.

The last procedure of serving contact lenses is the storing of contact lenses. 0.9% NaCl is commonly used for holding contact lenses in an enclosed container to prevent a contamination when carrying.

As indicated, a variety of apparatus have been disclosed for cleaning and sterilizing contact lenses, and have appeared on the market. However, they still have drawbacks, and cannot fully satisfy individual needs.

SUMMARY OF THE INVENTION

The present invention has been accomplished under the circumstances in view. It is one object of the present invention to provide an efficient and effective contact lens serving method which uses ultrasonic waves to clean contact lenses, and heat to disinfect contact lens solution medium. It is another object of the present invention to provide an efficient and effective contact lens serving apparatus which is compact, and easy to operate through the control of a fully automatic control circuit. It is still another object of the present invention to provide an efficient and effective contact lens serving apparatus which permits the contact lens serving container to be separated from the mainframe for easy carrying with oneself. It is still another object of the present invention to provide an efficient and effective contact lens serving apparatus which uses NaCl as contact lens solution medium for holding contact lenses for cleaning and disinfecting, and which permits NaCl to be repeatedly used. It is still another object of the present invention to provide an alternative ultrasonic energy source for an efficient and effective contact lens serving apparatus which produces ultrasonic waves of different frequencies at different times for effectively removing dirt of different particles from contact lenses. It is still another object of the present invention to provide ultrasonic generating means and heating source means for an efficient and effective contact lens serving apparatus which can be synchronously controlled to clean contact lenses and to heat the contact lens solution medium during cleaning so as to rapidly complete the cleaning and sterilization of the contact lenses.

According to the present invention, the method of cleaning and disinfecting contact lenses, including the step of transmitting a ultrasonic energy field toward a pair of contact lenses being suspended in a solution medium in a cleaning cup, causing a cavitation to be produced to remove dirt from the contact lenses, the step of keeping the solution medium to be maintained standing still in for about 3–5 minutes for permitting suspended substance to settle to the bottom of the solution medium, the step of using heating means to heat the solution medium to about 90° C. for about 15–20 minutes so as to disinfect bacteria and degrade toxic substance carried on the contact lenses, and the step of gradually cooling down the temperature of the solution medium to room temperature. The ultrasonic waves are preferably set within 20–30 Khz to provide an energy of about 1.5–3 W/cm$^2$, so that a definite cavitation is formed in the solution medium, causing the solution medium to produce micro-jets for removing dirt from the contact lenses. The ultrasonic cleaning step is performed for about 6–10 minutes, and then the solution medium is maintained still so that suspended dirt which is removed from the contact lenses can settle to the bottom of the solution medium for further disinfection. After the ultrasonic cleaning procedure, the heating means is controlled to heat the solution medium to 90° C. gradually. Because the temperature is increased gradually, the change of the temperature does not affect the physical structure of the contact lenses. When the solution medium is maintained at 90° C. for about 15–20 minutes, bacterial and toxic substance are completely killed or decomposed. This heating temperature does not cause the contact lenses to produce any structural (physical) change. Even if the contact lenses are made from PHEMA (poly-2-hydroxyethyl methacrylay) or organosilicon rubber, the heating temperature does not cause any bad effect. Tile solution medium can be 0.9% NaCl which is sterilized during the disinfecting procedure. Therefore, it is not necessary to replace the solution medium after each cleaning and disinfecting operation.

The apparatus for performing the aforesaid method of cleaning and disinfecting contact lenses comprises a housing which defines a top open chamber and a bottom chamber and having two metal contact plates bilaterally mounted in the top open chamber; a cylindrical ultrasonic wave guide mounted in the top open chamber of the housing; a graduated cleaning cup mounted in the ultrasonic wave guide and having an outer thread disposed outside the ultrasonic wave guide, a solution medium contained in the graduated cleaning cup; a lens holder mounted in the graduated cleaning cup, the lens holder comprising a case-like holder base suspended in the graduated cleaning cup, and two lens suspending devices mounted on two opposite side walls of the holder base and adapted for holding a respective contact lens, the lens suspending devices having different colors, each of the two opposite side walls of the holder base having a grille through which the solution medium passes in and out, the suspending devices being pivoted to the two opposite side walls of the holder base and having a respective semi-spherical grille respectively covered over tile grilles of the holder base; a heating rod suspended in the case-like holder base of the lens holder and having two electrodes; a top cap adapted for coverage of the cleaning cup over the lens holder and the heating rod, the top cap comprising an inner thread threaded onto the outer thread of the cleaning cup, two contact metal plates respectively disposed in contact with the electrodes of the heating rod and the metal contact plates of the housing; and a control circuit mounted in the bottom chamber of the housing; the control circuit comprising a microprocessor connected to the metal contact plates of the housing for controlling the heating rod to heat the solution medium to 90° C. for about 15–20 minutes, a ultrasonic speaker mounted on the ultrasonic wave guide at a bottom side thereof and controlled by the microprocessor to provide a ultrasonic energy field of frequency bout 20–30 Khz and of energy about 1.5–3 W/cm$^2$ for about 6–10 minutes to clean the contact lenses, a first control switch adapted for controlling the microprocessor to stop the operation, a second control switch adapted for controlling the microprocessor to turn on the ultrasonic speaker, a third control switch adapted for controlling the microprocessor to turn on the heating rod, and a fourth control switch adapted for controlling the microprocessor to turn on the ultrasonic speaker and the heating rod through a predetermined automatic serving operation procedure, and four indicator lights respectively coupled to the control switches.

When the fourth control switch is pressed on to start the automatic serving operation, the microprocessor of the control circuit board gives an instruction through turn on an ultrasonic oscillating circuit (ultrasonic speaker), and at the same time a ultrasonic cleaning control counter starts to count, and therefore the contact lenses are cleaned by ultrasonic waves. The ultrasonic working time is set at for example 8 minutes. When the predetermined length of ultrasonic working time is up, the ultrasonic cleaning control counter gives a signal to cut off power supply from the ultrasonic speaker. When the ultrasonic speaker is stopped, a sedimentation control counter starts to count a predetermined length of sedimentation time. This sedimentation time is set for example at 7 minutes. Within this sedimentation time, suspended substance settles to the bottom of the solution medium to prevent a secondary pollution to the contact lenses. When the sedimentation time is up, the heating rod is turned on to heat the solution medium gradually to 90° C., anti at the same time a disinfecting control counter starts to count. When the temperature of the solution medium reaches 90° C., it is maintained at the 90° C. for about 20 minutes. When this predetermined disinfecting time is up, the corresponding counter gives a signal to the microprocessor, causing it to stop the operation of the heating rod. When the heating rod is turned off after the disinfecting mode, the temperature of the solution medium drops gradually to room temperature, and the auto-serving operation is done. In the aforesaid structure, the housing and the ultrasonic wave guide are assembled together to form a mainframe unit. The cleaning cup, the lens holder, the heating rod, and the top cap are assembled together to form a serving container unit adapted for detachably mounting in the ultrasonic wave guide of the mainframe unit. Therefore, the serving container unit can be separately used for carrying the contact lenses with oneself. When the fourth control switch is switched on to start the automatic serving operation procedure, a length of time about 3–5 minutes is executed between the termination of the operation of the ultrasonic speaker and before the operation of the heating rod, to maintain the solution medium still for permitting suspended substance to settle to the bottom of the solution medium.

Furthermore the holder base of the lens holder holds the heating rod and the lens suspending devices in the solution medium, and is spaced above the bottom wall of the cleaning cup at a distance for permitting suspended substance to settle to the bottom of the solution medium.

As an alternate form of the present invention, the ultrasonic wave generator (the ultrasonic speaker) and the heating rod may be installed in the ultrasonic wave guide to simplify the structure of the apparatus. In order to reduce the installation space, an electric heating wire may be used instead of the heating rod.

DETAILED DESCRIPTION OF THE PREFERRED EMBODIMENT

Figure 1:
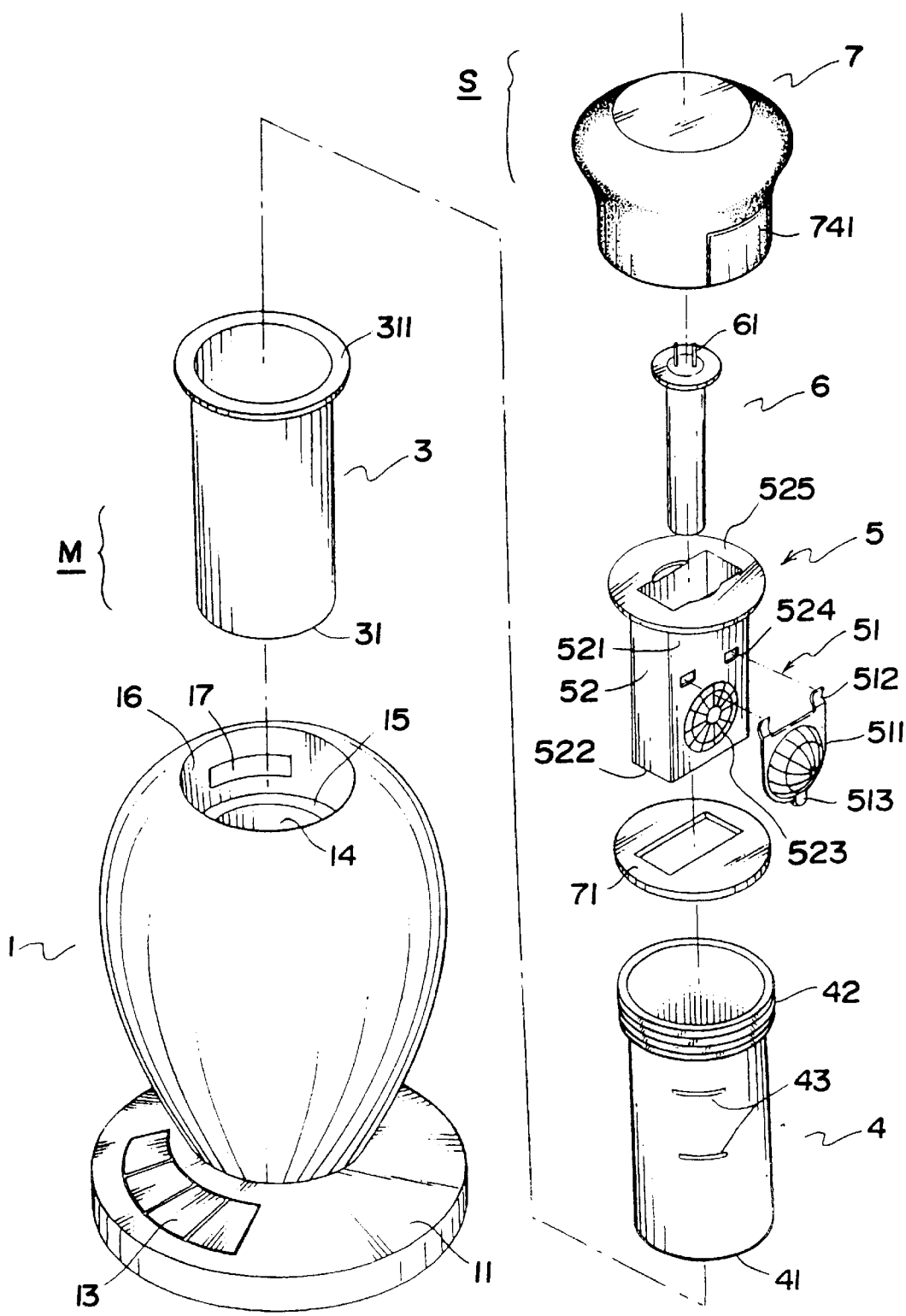
FIG. 1 is an exploded view of an apparatus for cleaning and disinfecting contact lenses according to the present invention.
Figure 2:
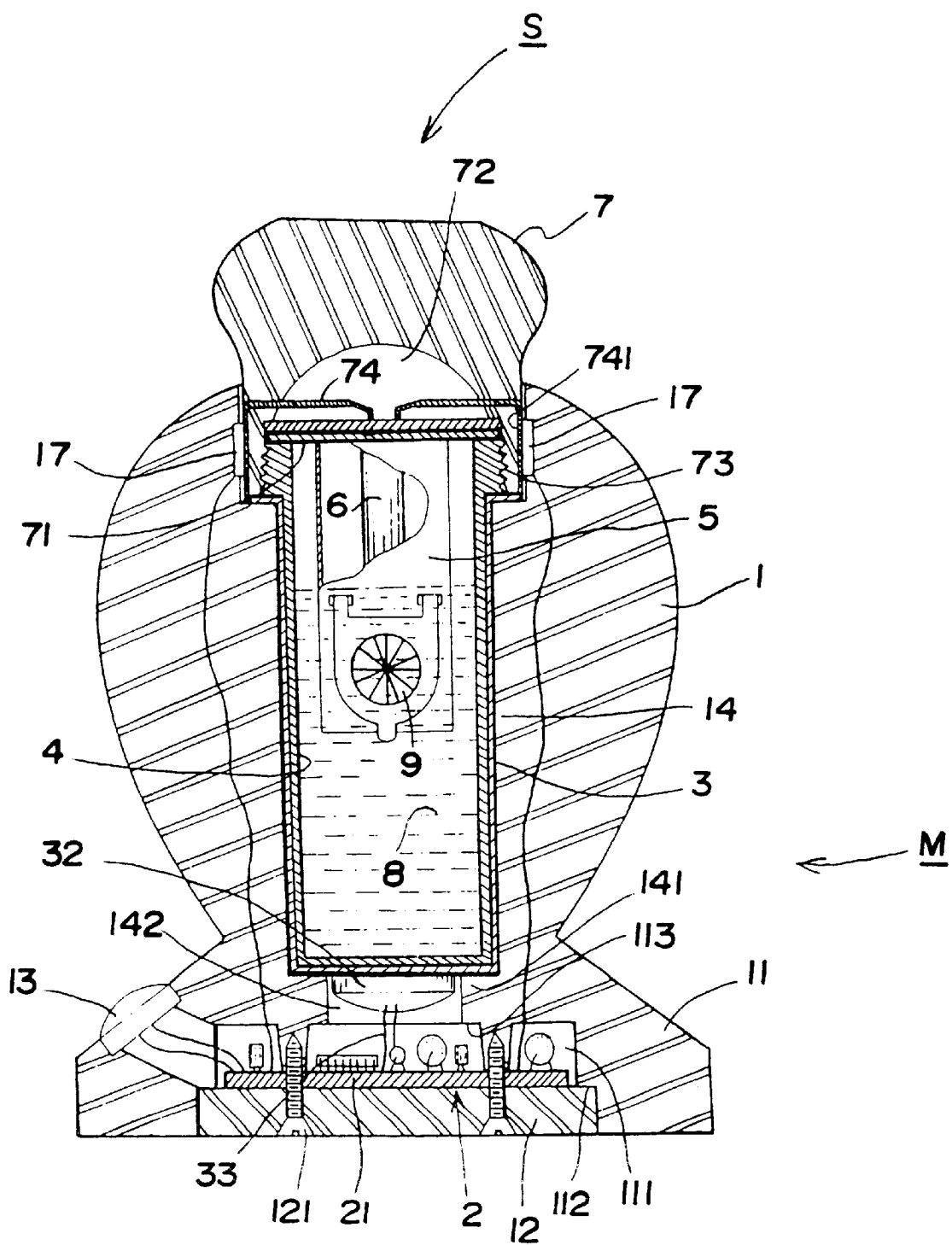
FIG. 2 is a side view in section of the apparatus shown in FIG. 1.

Referring to FIGS. 1 and 2, an apparatus for cleaning and disinfecting contact lenses in accordance with the present invention is generally comprised of a mainframe unit M, and a servicing container unit S. The mainframe unit M comprises a housing 1, a control circuit assembly 2, and a ultrasonic wave guide 3. The housing 1 has broad bottom 11 defining a bottom chamber 111 adapted for holding the substrate board 21 of the control circuit assembly 2 and the related electronic elements. The bottom chamber 111 has a shoulder 112. A bottom cover 12 is mounted on the shoulder 112 within the bottom chamber 111 and disposed in flush with the bottom side of tie bottom 11. Screws 121 are fastened to the top wall 113 of the bottom chamber 111 to secure the control circuit assembly 2 and the bottom cover 12 together. An ultrasonic sealing method may be employed to fasten the bottom cover 12 to the shoulder 112. A set of waterproof, press control type control switches 13 is mounted on the bottom 11 of the housing 1 and respectively connected to the control circuit assembly 2. These control switches 13 include at least four operation mode control switches for controlling the modes of STOP, AUTO SERVICE, CLEAN, and DISINFECT. The housing 1 further comprises a stepped top open chamber 14 having a step 15 and a mouth 16 above the step 15. The bottom wall 141 of the top open chamber 14 has a wire hole 142 disposed in communication with the bottom chamber 111. Two metal contact plates 17 are symmetrically mounted in the mouth 16 at two opposite sides and respectively connected to the control circuit assembly 2 by a respective conductor (not shown). The exposed part of each metal contact plate 17 is deformable. The substrate board 21 of the control circuit assembly 2 is fixedly mounted in the bottom chamber 111 The control circuit assembly 2 has a power cord extending out of the housing 1 (not shown) for connection to a power supply. The ultrasonic wave guide 3 is preferably made from stainless steel in the shape of a cylindrical cup fitting the top open chamber 14 of the housing 1, having an outward top flange 311 around the periphery of the top open side thereof, and a ultrasonic speaker (vibrator) 32 welded to the bottom wall 31 thereof. When the ultrasonic wave guide 3 is mounted in the top open chamber 14 of the housing 1, the outward top flange 311 is supported on and fixedly secured to the step 15. The ultrasonic wave guide 3 can be fastened to the top open chamber 14 of the housing 1 with a bonding agent, or by means of any of a variety of conventional mounting techniques such as screw joint, rivet joint, etc. The speaker 32 has a pair of conductors 33 inserted through the wire hole 142 in the bottom wall 141 of the top open chamber 14, and then connected to the circuit board assembly 2. The speaker 32 is preferably made from ferrite or nickel. The frequency of the speaker 32 is defined within 10–59 kHz.

The serving container unit S is comprised of a cleaning cup 4, a lens holder 5, a heating rod 6, and a top cap 7. The cleaning cup 4 is made from transparent, heat-resisting (heating resisting property over 120° C.) adapted for fitting into the ultrasonic wave guide 3. When the cleaning cup 4 is mounted in the ultrasonic wave guide 3, the bottom wall 41 of the cleaning cup 4 is closely disposed in contact with the bottom wall 31 of the ultrasonic wave guide 3 so that ultrasonic waves can be efficiently transmitted to the inside of the cleaning cup 4. The cleaning cup 4 has an outer thread 42 around the periphery disposed outside the ultrasonic wave guide 3 for the mounting of the top cap 7. Graduations 43 are made on the periphery of the cleaning cup 4 for the indication of the volume of the solution medium filled.

The lens holder 5 comprises a case-like holder base 52, and two lens suspending devices 51 mounted on two opposite side walls 521 of the holder base 52 and adapted for holding a respective contact lens. The lens suspending devices 51 preferably have different colors so that the user can quickly distinguish the lens for the left eye from the lens for the right eye. Each of the side walls 521 of the holder base 52 has a grille 523 through which the solution medium passes, and two coupling holes 524 spaced above the grille 523. Each of the suspending devices 51 comprises a semi-spherical grille 511 covered over the grille 523 of the corresponding side wall 521, two coupling lugs 512 respectively and pivotably coupled to the coupling holes 524 of the corresponding side wall 521, and a snap 513 adapted for fastening to the bottom wall 522 of the holder base 52. The heating rod 6 is suspended in the holder base 52 of the lens holder 5, having two electrodes 61 at the top.

The top cap 7 comprises a bottom chamber 72 adapted for receiving the outward top flange 525 of the lens holder 5 and the top end of the cleaning cup 4, an inner thread 73 formed in the bottom chamber 72 and threaded onto the outer thread 42 of the cleaning cup 4, and two metal contact plates 74 disposed inside the bottom chamber 72 and forced into contact with the electrodes 61 of the heating rod 6 respectively. The metal contact plates 74 have a respective extension portion 741 disposed outside the top cap 7 and fixedly secured to the outside wall thereof. The extension portions 741 of the metal contact plates 74 are spaced from each other. Furthermore, a rubber gasket 71 is mounted around the holder base 52 of the lens holder 5, and retained between the topmost edge of the cleaning cup 4 and the outward top flange 525 of the lens holder 5.

In the serving container unit S, the holder base 52 is made in such a length that the lens suspending devices 51 and the electrode 6 can be suspending in the solution medium 8. When the lens holder 5 is installed in the cleaning cup 4, the bottom wall 522 of the lens holder 5 is spaced from the bottom wall 41 of the cleaning cup 4 at a certain distance. Furthermore, when the serving container unit S and the mainframe unit M are assembled, the extension portions 741 of the metal contact plates 74 of the top cap 7 are forced into contact with the metal contact plates 17 of the housing 1 respectively, so that signal an be transmitted from the control circuit board 2 to the heating rod 6, causing it to produce heat.

When in use, dirty contact lenses 9 are respectively mounted inside the lens suspending devices 51 of the lens holder 5, then a suitable volume of the solution medium 8 is filled into the cleaning cup 4 subject to the indication of the graduations 43. The solution medium is preferably about 0.9% NaCl. When the solution medium 8 is filled in the cleaning cup 4, the serving container unit S is assembled and then mounted in the ultrasonic wave guide 3 of the mainframe unit M, permitting the bottom wall 41 of the cleaning cup 4 to be closely attached to the bottom wall 31 of the ultrasonic wave guide 3 and the extension portions 741 of the metal contact plates 74 of the top cap 7 to be forced into contact with the metal contact plates 17 of the housing 1 respectively. When assembled, the power cord is connected to the electric power supply socket (not shown). Thus, the apparatus has been ready For serving.

Figure 3:
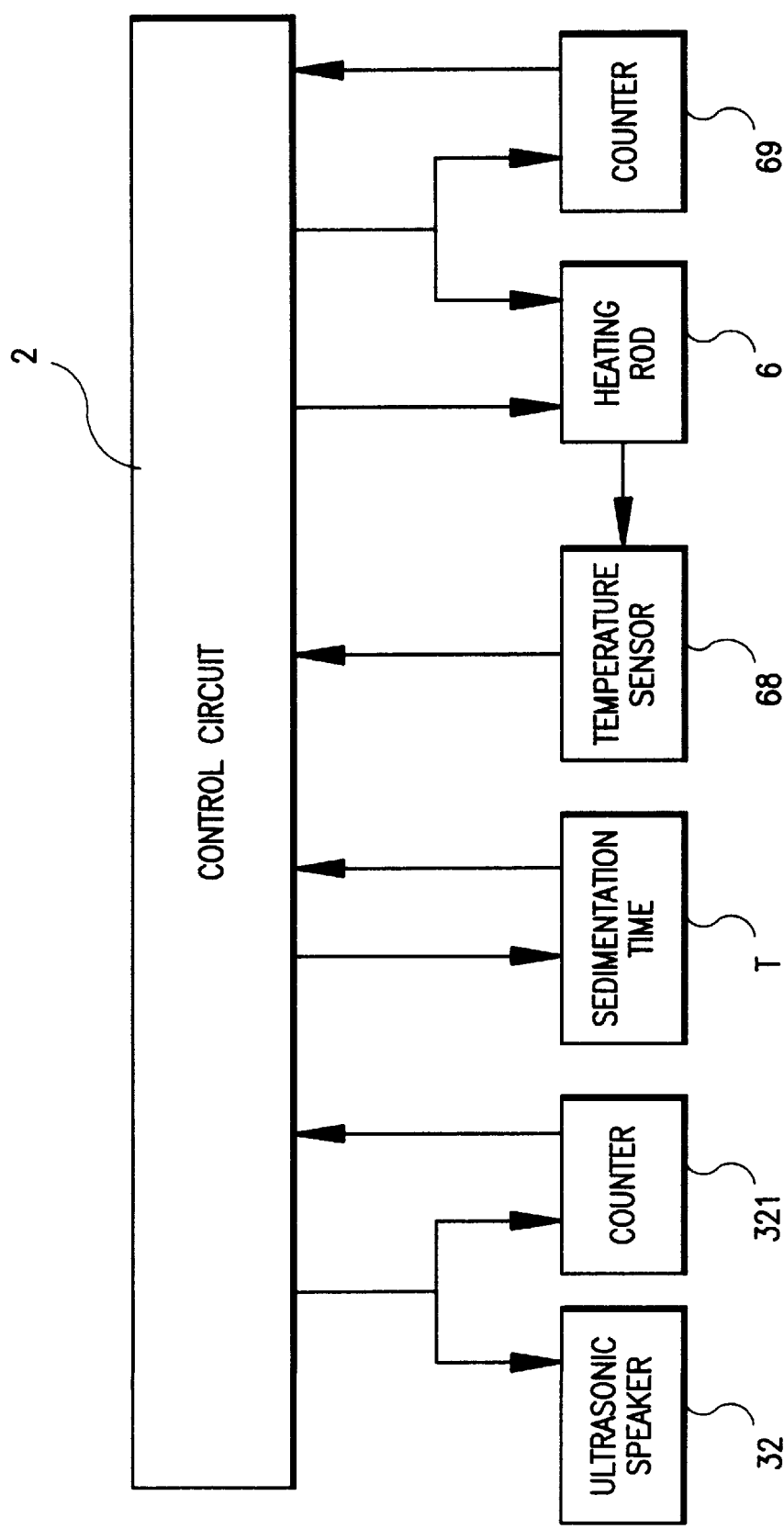
FIG. 3 is a control block diagram showing the control flow of the present invention.
Figure 4:
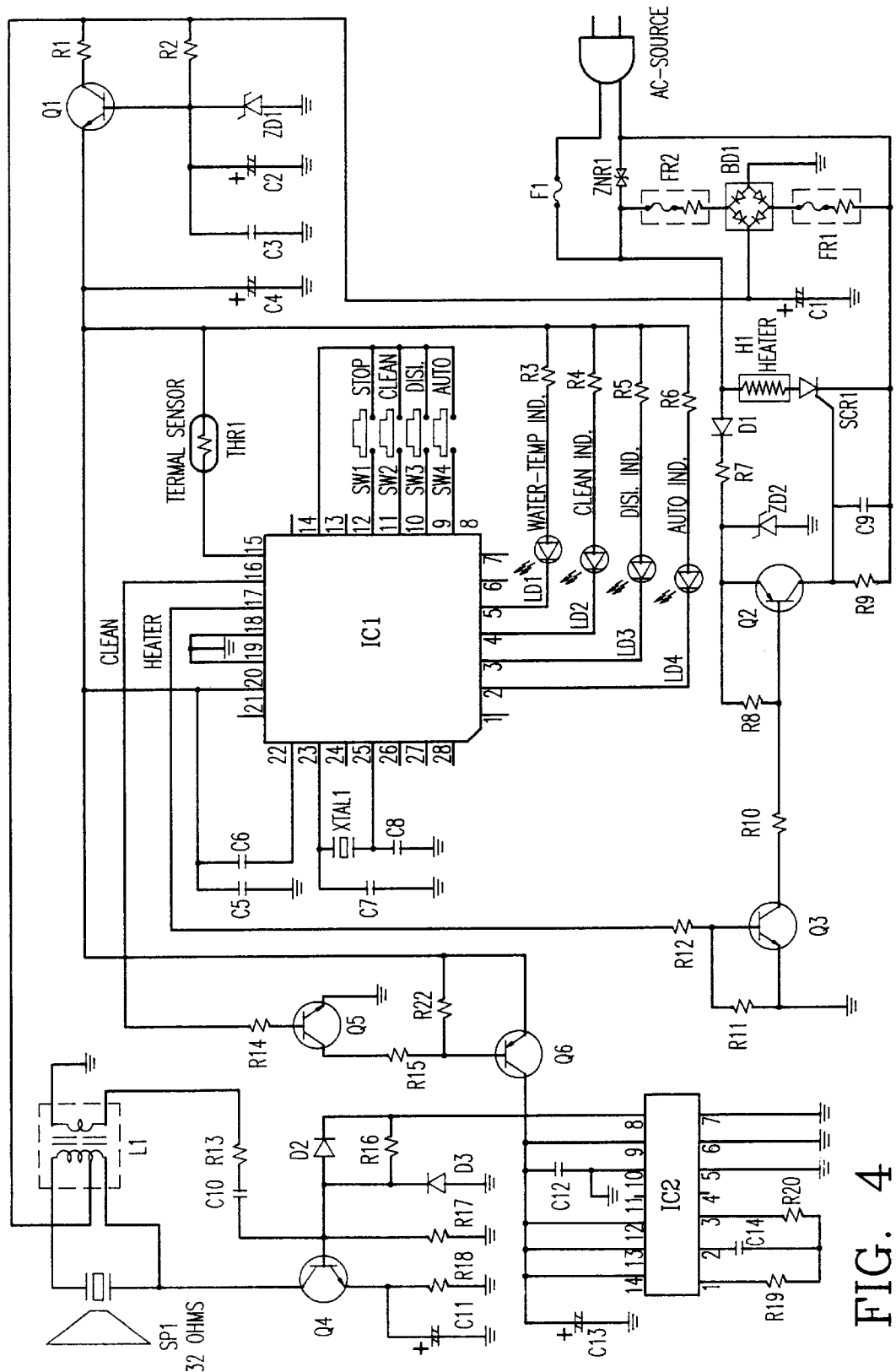
FIG. 4 is a circuit diagram of the control circuit board of the present invention.

Referring to FIGS. 3 and 4, the press control type control switches 13 include a first control switch SW1 for stop control, a second control switch SW2 for cleaning control, a third control switch SW3 for disinfecting control, and a fourth control switch SW4 for auto-serving control. There are indicator lights corresponding to the control switches 13, namely, the first indicator light LD1 for the indication of end of disinfecting, the second indicator light LD2 for the indication of under cleaning mode, the third indicator light LD3 for the indication of under disinfecting mode, and the fourth indicator light LD4 for the indication of under auto-serving mode. When the fourth control switch SW4 is pressed on, IC1 gives an instruction through Q5 to drive a ultrasonic oscillating circuit, which is comprised of IC2 and Q4, and at the same time IC1 starts to count, L1 is coupled to the ultrasonic speaker 32, causing the ultrasonic speaker 32 to produce a sound field of about 30 Khz, 3 W/cm$^2$, so that a definite cavitation is formed in the cleaning cup 4, causing micro jets to be produced and acted on the contact lenses 9. Therefore, the dirty substance is removed from the contact lenses 9. When IC1 starts to work, its ultrasonic working time control counter 321 starts to count. The ultrasonic working time is set at for example 8 minutes. When the predetermined length of ultrasonic working time is up, the counter 321 of IC1 gives a signal to Q6, causing it to cut off power supply, and therefore IC2 stops the operation of the ultrasonic speaker 32. When the ultrasonic speaker 32 is stopped, IC1 starts to count a predetermined length of sedimentation time T, this sedimentation time T is set for example at 7 minutes. Within this sedimentation time T, suspended substance settles to the bottom of the cleaning cup 4 to prevent a secondary pollution to the contact lenses 9. When the sedimentation time T is up, IC1 gives a signal through the metal contact plates 17, 74 to a silicon controlled rectifier SCR1, causing it to turn on the heating rod 6 so as to disinfect the contact lenses 9, and at the same time a disinfecting control counter 69 starts to count. When the heating rod 6 is turned on, it produces heat to heat the solution medium 8 to about 90° C. When the temperature of the solution medium 8 reaches 90° C., a temperature sensor (THR1) 68 is induced to give a signal to IC1, causing it to turn off SCR1, and therefore the solution medium 8 is maintained at 90° C. to disinfect the contact lenses 9. The length of the disinfecting time is set at 20 minutes. When this predetermined disinfecting time is up, the corresponding counter 69 gives a signal to IC1, causing it to stop the operation of the heating rod 6. When the heating rod 6 is turned off after the disinfecting mode, the temperature of-the solution medium 8 drops gradually to room temperature, and the auto-serving operation is done.

During the disinfecting mode, the solution medium 8 is simultaneously disinfected by heat, therefore the solution medium 8 can be repeatedly used to serve the contact lenses 9.

When going outdoors, the serving container unit S can be separated from the mainframe unit M and carried with oneself to hold one's contact lenses on the inside. Because the lens suspending devices 51 are immovable during the cleaning and disinfecting process, the contact lenses will not be scratched or damaged.

While only one embodiment of the present invention has been shown and described, it will be understood that various modifications and changes could be made thereunto without departing from the spirit and scope of the invention disclosed. For example, an alternative ultrasonic wave generator may be used to provide ultrasonic waves for cleaning contact lenses; the ultrasonic wave generating means and the heating type disinfecting means may be synchronously operated to clean and to disinfect contact lenses; the ultrasonic wave generating means and the heating type disinfecting means may be installed in the ultrasonic wave guide to simplify the structure.

What the invention claimed is:

1. An apparatus for cleaning and disinfecting contact lenses comprising:

a housing defining a top open chamber and a bottom chamber, said housing having two metal contact plates bilaterally mounted opposite each other in said top open chamber;

a cylindrical ultrasonic wave guide mounted in said top open chamber of said housing;

a graduated cleaning cup detachably mounted in said ultrasonic wave guide, said graduated cleaning cup having an outer thread residing above said ultrasonic wave guide when said graduated cleaning cup is inserted into said ultrasonic wave guide;

a lens holder mounted in said graduated cleaning cup, said lens holder including an outward top flange sitting on top of said graduated cleaning cup, a holder base depending from said outward top flange into said graduated cleaning cup, and two lens suspending devices respectively mounted on two opposite side walls of said holder base for holding a contact lens, each of the two opposite side walls of said holder base having a grill through which a solution medium passes, each of said lens suspending devices pivotally connected to the respective opposite side wall of said holder base and each of said lens suspending devices having a respective semi-spherical grill overlaying the grill of said holder base;

a heating rod suspended in said holder base of said lens holder, said heating rod having two electrodes;

a top cap connected to said graduated cleaning cup, said top cap including an inner thread to threadingly engage said outer thread of said cleaning cup and two contact metal plates respectively disposed in contact with said two electrodes of said heating rod and said two metal contact plates of said housing; and a control circuit mounted in said bottom chamber of said housing, said control circuit including p2 a microprocessor connected to said two metal contact plates of said housing for controlling said heating rod to heat the solution medium to 90° C. for about 15–20 minutes, an ultrasonic speaker mounted to a bottom side of said ultrasonic wave guide, said ultrasonic speaker controlled by said microprocessor to provide an ultrasonic energy field in a frequency range of about 20–30 khz with an energy of about 1.5–3 W/cm$^2$ for about 6–10 minutes to clean contact lenses held by said lens suspending devices, a first control switch to stop the operation of said microprocessor, a second control switch to control said microprocessor to turn on said ultrasonic speaker, a third control switch to control said microprocessor to turn on said heating rod, a fourth control switch to control said microprocessor to turn on said ultrasonic speaker and said heating rod through a predetermined automatic operation procedure, a first indicator light coupled to said first control switch, a second indicator light coupled to said second control switch, a third indicator light coupled to said third control switch, and a fourth indicator light coupled to said fourth control switch.

2. The apparatus of claim 1, wherein said housing and said ultrasonic wave guide form a mainframe unit, and said cleaning cup, said lens holder, said heating rod, and said top cap form a serving container unit detachably mounted in said ultrasonic wave guide of said mainframe unit.

3. The apparatus of claim 1, wherein when said fourth control switch is switched on to start said automatic operation procedure, a length of time of about 3–5 minutes elapses between the termination of the operation of said ultrasonic speaker and before the operation of said heating rod to maintain the solution medium in a still state to permit suspended substances to settle to the bottom of said graduated cleaning cup.

4. The apparatus of claim 1, wherein said holder base of said lens holder holds said heating rod and said lens suspending devices in the solution medium, and said lens suspending devices are spaced above the lowest edge of said graduated cleaning cup at a distance for permitting suspended substances to settle to the bottom of said graduated cleaning cup.

5. The apparatus of claim 1 wherein each of said lens suspending devices have a different color.

* * * * *